US011432778B2

(12) United States Patent
Samiee

(10) Patent No.: US 11,432,778 B2
(45) Date of Patent: Sep. 6, 2022

(54) METHODS AND SYSTEMS FOR PATIENT MONITORING

(71) Applicant: General Electric Company, Schenectady, NY (US)

(72) Inventor: Kaveh Samiee, Helsinki (FI)

(73) Assignee: General Electric Company, Schenectady, NY (US)

(*) Notice: Subject to any disclaimer, the term of this patent is extended or adjusted under 35 U.S.C. 154(b) by 957 days.

(21) Appl. No.: 15/413,779

(22) Filed: Jan. 24, 2017

(65) Prior Publication Data

US 2018/0206797 A1 Jul. 26, 2018

(51) Int. Cl.
*A61B 5/00* (2006.01)
*G16H 40/67* (2018.01)
(Continued)

(52) U.S. Cl.
CPC ............ *A61B 5/746* (2013.01); *A61B 5/7264* (2013.01); *A61B 5/7275* (2013.01); *G16H 40/67* (2018.01); *A61B 5/0022* (2013.01); *A61B 5/01* (2013.01); *A61B 5/021* (2013.01); *A61B 5/024* (2013.01); *A61B 5/14532* (2013.01);
(Continued)

(58) Field of Classification Search
CPC ..... A61B 5/746; A61B 5/7264; A61B 5/0402; A61B 5/0201; A61B 5/024; A61B 5/0022; A61B 5/01; A61B 5/7267; A61B 5/7275; A61B 5/14532; A61B 5/318; A61B 5/021; A61B 5/14542; G16H 40/67
See application file for complete search history.

(56) References Cited

U.S. PATENT DOCUMENTS 5,251,626 A * 10/1993 Nickolls ............ A61N 1/36514
607/14
5,463,548 A * 10/1995 Asada .................. G06N 3/0454
600/300
(Continued)

FOREIGN PATENT DOCUMENTS

WO          9103979 A1      4/1991
WO    WO-2015185706 A1 *  12/2015

OTHER PUBLICATIONS

Definition of concatenate. Merriam-Webster, retrieved on May 15, 2021; Retrieved from the Internet: <https://www.merriam-webster.com/dictionary/concatenate> (Year: 2021).*
(Continued)

*Primary Examiner* — Gary Jackson
*Assistant Examiner* — Sebastian X Lukjan
(74) *Attorney, Agent, or Firm* — McCoy Russell LLP

(57) ABSTRACT

Systems and methods are provided for false alarm suppression in patient monitoring systems. In one embodiment, a method comprises inputting each electronic signal of a plurality of electronic signals into a corresponding predictor cloud of a plurality of predictor clouds, each predictor cloud comprising a long short-term memory neural network and a recurrent neural network, and responsive to an alarm generated based on at least one of the plurality of electronic signals, suppressing the alarm responsive to outputs of the plurality of predictor clouds indicating the alarm is false. In this way, patient monitors may be more reliable with fewer false alarms.

15 Claims, 4 Drawing Sheets

(51) Int. Cl.
*A61B 5/024* (2006.01)
*A61B 5/021* (2006.01)
*A61B 5/145* (2006.01)
*A61B 5/01* (2006.01)
*A61B 5/318* (2021.01)

(52) U.S. Cl.
CPC ............ *A61B 5/14542* (2013.01); *A61B 5/318* (2021.01); *A61B 5/7267* (2013.01)

(56) References Cited

U.S. PATENT DOCUMENTS

| | | | |
|---|---|---|---|
| 5,745,034 | A | 4/1998 | Andersen et al. |
| 6,801,802 | B2 | 10/2004 | Sitzman et al. |
| 7,450,986 | B2 * | 11/2008 | Nguyen ................ A61B 5/00 600/513 |
| 8,155,734 | B2 * | 4/2012 | Li ...................... A61B 5/0205 600/515 |
| 8,214,314 | B2 | 7/2012 | Bonissone et al. |
| 8,457,706 | B2 * | 6/2013 | Baker, Jr. ........... A61B 5/14551 600/323 |
| 9,015,093 | B1 | 4/2015 | Commons |
| 2005/0015009 | A1 * | 1/2005 | Mourad .............. A61B 5/7267 600/438 |
| 2007/0213599 | A1 * | 9/2007 | Siejko .................. A61B 5/00 600/300 |
| 2016/0235372 | A1 * | 8/2016 | Schneider ........... A61B 5/0075 |
| 2016/0299938 | A1 * | 10/2016 | Malhotra ............ G06N 3/0445 |
| 2017/0206464 | A1 * | 7/2017 | Clayton .............. G06N 3/0454 |
| 2017/0249445 | A1 * | 8/2017 | Devries ................ G16H 20/60 |
| 2018/0060507 | A1 * | 3/2018 | Ning ..................... G16H 50/50 |
| 2021/0022688 | A1 * | 1/2021 | Lee ..................... G16H 80/00 |

OTHER PUBLICATIONS

Defintion of concatenation. Wikkipedia, retrieved on Aug. 30, 2021; Retrieved from the Internet <https://en.wikipedia.org/wiki/Concatenation> (Year: 2021).*

Lawless, S., "Crying wolf: False alarms in a pediatric intensive care unit," Critical Care Medicine, vol. 22, No. 6, Jun. 1994, 5 pages.

Gers, F., "Long Short-Term Memory in Recurrent Neural Networks," PhD Thesis, Ecole Polytechnique Federate de Lausanne, Available as Early as Jan. 1, 2001, 102 pages.

"IntelliRate Technology for Patient Monitoring," GE Healthcare Brochure, Available Online at http://www3.gehealthcare.pl/~/media/downloads/uk/product/intensive%20care/brochure%20-%20intellirate%20technology%20for%20patient%20monitoring.pdf?Parent=%7B0E27EAC2-EEA0-4592-AC38-FDBD538CCDA3%7D, Aug. 2010, 4 pages.

"Dash 3000/4000/5000tm Patient Monitor Service Manual," GE Healthcare Manual, Available Online at http://www3.gehealthcare.com/~/media/downloads/us/services/equipment%20services/support-center/daylight-savings-time/patient-monitoring/monitors/gehc-service-manual_dash-3000-4000-5000-patient-monitor_v7.pdf, Apr. 22, 2013, 282 pages.

Lehman, L. et al., "A Physiological Time Series Dynamics-Based Approach to Patient Monitoring and Outcome Prediction," IEEE Journal of Biomedical and Health Informatics, vol. 19, No. 3, May 2015, Published Online Jun. 30, 2014, 9 pages.

"American Epilepsy Society Seizure Prediction Challenge," Kaggle Website, Available Online at https://www.kaggle.com/c/seizure-prediction, Competition Launched Aug. 25, 2014, 4 pages.

"Reducing False Arrhythmia Alarms in the ICU: the PhysioNet/Computing in Cardiology Challenge 2015," PhysioNet Website, Available Online at https://www.physionet.org/challenge/2015/, Competition Launched Feb. 16, 2015, 14 pages.

Clifford, G. et al., "The PhysioNet/Computing in Cardiology Challenge 2015: Reducing False Arrhythmia Alarms in the ICU," Proceedings of the Computing in Cardiology Conference (CinC 2015), Sep. 6, 2015, Nice, France, 4 pages.

Lipton, Z. et al., "Learning to Diagnose with LSTM Recurrent Neural Networks," Proceedings of the International Conference on Learning Representations (ICLR 2016), May 2, 2016, Available Online Mar. 1, 2016, San Juan, Puerto Rico, 18 pages.

Zong, W. et al., "A practical algorithm to reduce false critical ECG alarms using arterial blood pressure and/or photoplethysmogram waveforms," Physiological Measurement, vol. 37, No. 8, Aug. 2016, Published Online Jul. 25, 2016, 15 pages.

"Melbourne University AES/MathWorks/NIH Seizure Prediction," Kaggle Website, Available Online at https://www.kaggle.com/c/melbourne-university-seizure-prediction, Competition Launched Sep. 2, 2016, 3 pages.

* cited by examiner

METHODS AND SYSTEMS FOR PATIENT MONITORING

FIELD

Embodiments of the subject matter disclosed herein relate to patient monitoring, and more particularly, to false alarm suppression in patient monitoring systems.

BACKGROUND

Patient monitors routinely process signals acquired from patients and provide a caregiver or clinician with computed estimates of features contained within those signals. In the case of ECG (electrocardiogram) signals, those features include heart rate and arrhythmias (i.e., disturbances in the normal cardiac rhythm).

One function of a patient monitor is to provide alarm mechanisms to alert the user when the patient's heart rate is outside of prescribed limits, or when arrhythmias occur. However, the presence of noise in the acquired ECG signal, due to a multiplicity of causes, results in a significant false positive alarm rate for these alarm conditions. Such false alarm rates decrease clinician productivity and satisfaction, and decrease the effectiveness of clinical alarm mechanisms.

BRIEF DESCRIPTION

In one embodiment, a method comprises inputting each electronic signal of a plurality of electronic signals into a corresponding predictor cloud of a plurality of predictor clouds, each predictor cloud comprising a long short-term memory neural network and a recurrent neural network, and responsive to an alarm generated based on at least one of the plurality of electronic signals, suppressing the alarm responsive to outputs of the plurality of predictor clouds indicating the alarm is false. In this way, patient monitors may be more reliable with fewer false alarms.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
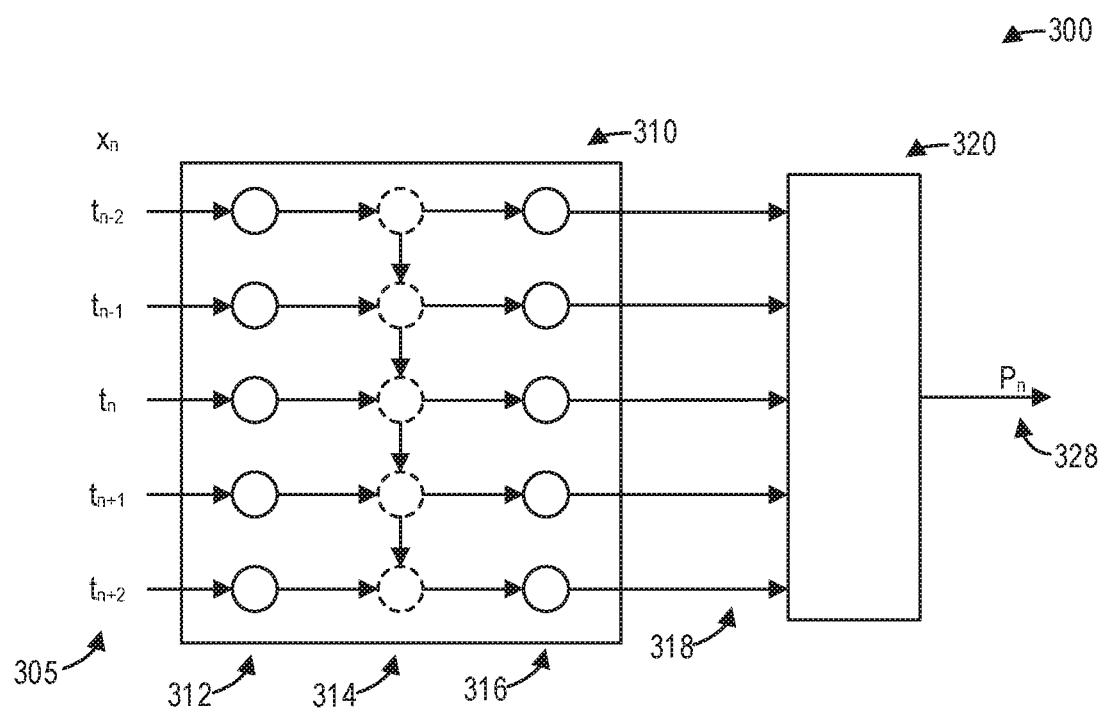
FIG. 3 shows a block diagram illustrating an example predictor cloud for analyzing an electronic signal from a patient monitoring device according to an embodiment.
Figure 4:
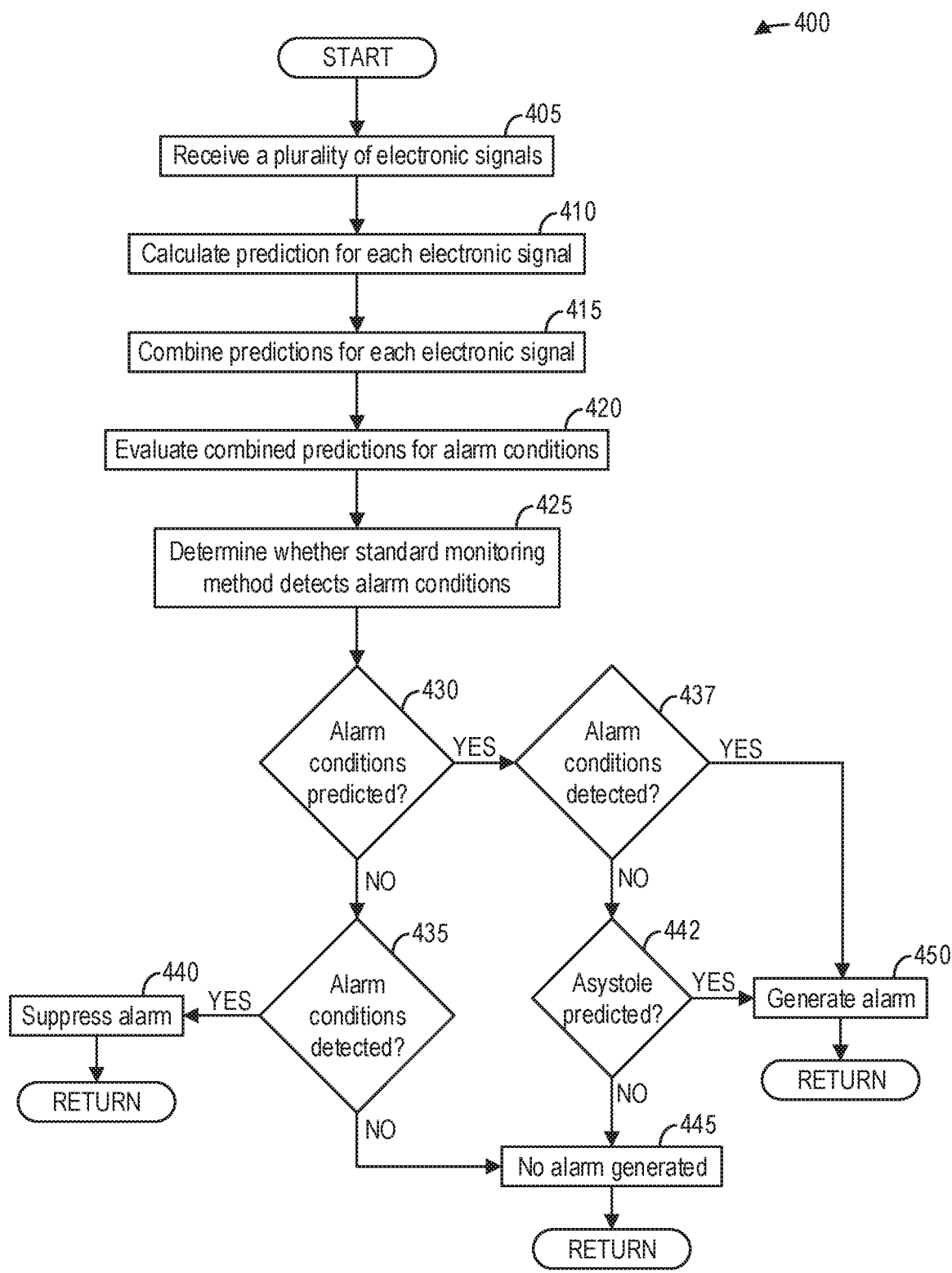
FIG. 4 shows a high-level flow chart illustrating an example method for suppressing false alarms according to an embodiment.

The following description relates to various embodiments of patient monitors. In particular, systems and methods are provided for false alarm suppression in patient monitoring systems. A patient monitoring system, such as the system depicted in FIGS. 1 and 2, may monitor various physiological traits of a patient in a health care facility such as, for example, an intensive care unit (ICU). A plurality of predictor clouds, such as the predictor cloud depicted in FIG. 3, are configured to predict the expected value of each monitored physiological trait. Since a low signal quality or environmental interference may degrade the confidence of an alarm generated based on one or more of the monitored physiological traits, the use of deep learning techniques to predict what the monitored traits should be enables the suppression of false alarms caused by said signal quality or interference. A method for utilizing the false alarm suppression system in conjunction with a standard alarm method is depicted in FIG. 4.

Figure 1:
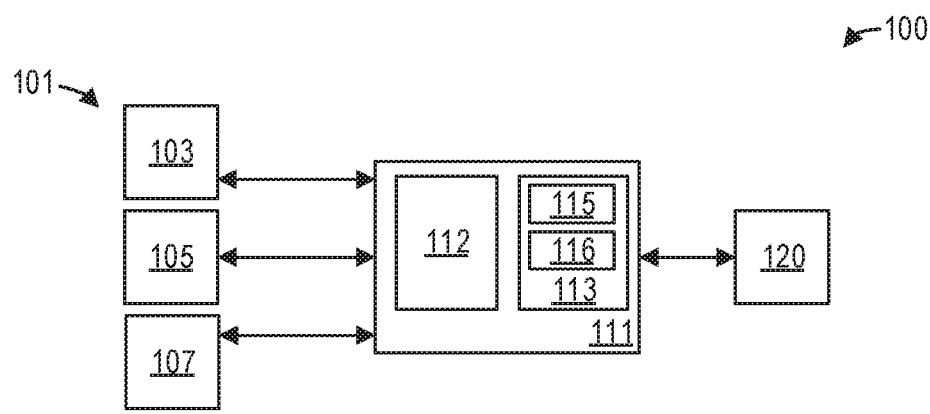
FIG. 1 shows a block diagram illustrating an example patient monitoring system.

FIG. 1 shows a block diagram illustrating an example patient monitoring system 100 for use in health care facilities. System 100 may comprise at least part of a patient monitor for monitoring one or more physiological traits (e.g., heart rate, respiratory rate, blood sugar levels, blood cell count, etc.) of a patient (not shown).

To that end, patient monitoring system 100 includes a plurality of patient monitoring devices 101, including a first monitoring device 103, a second monitoring device 105, and a third monitoring device 107. Each monitoring device of the plurality of patient monitoring devices 101 may be configured to monitor a different physiological trait of the patient. The patient monitoring devices may include, but are not limited to, an invasive and/or non-invasive blood pressure monitoring device, a pulse-oximetry monitoring device, a temperature monitoring device, a carbon dioxide monitoring device, a respiration monitoring device, a cardiac output monitoring device, and so on.

Patient monitoring system 100 further includes a computing device 111 communicatively coupled to each of the plurality of patient monitoring devices 101. The plurality of patient monitoring devices 101 provide measurements of physiological characteristics of a patient to a computing device 111.

Computing device 111 includes a processor 112 and non-transitory memory or storage device 113. The various methods and processes described further herein may be stored as executable instructions in the non-transitory memory 113 of the computing device 111 in system 100. For example, a standard monitoring module 115 and a predictor cloud monitoring module 116 may be stored as executable instructions in the non-transitory memory 113 that when executed cause the processor 112 to carry out specific methods and processes as described further herein.

Computing device 111 is also communicatively coupled to a display device 120. Display device 120 may be configured to display an alarm, in some examples, generated by the computing device 111.

The number of monitoring devices depicted is exemplary and non-limiting, as it should be appreciated that in some examples the plurality of patient monitoring devices 101 may include a number of monitoring devices greater than three or fewer than three.

Figure 2:
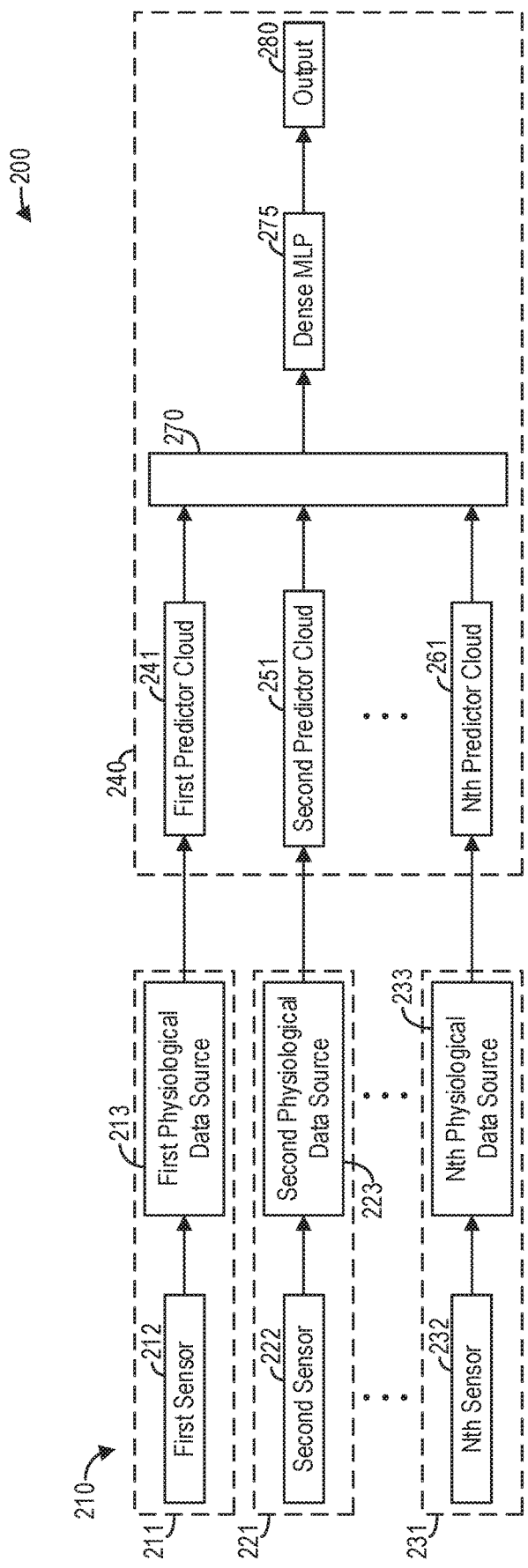
FIG. 2 shows a block diagram illustrating an example system for suppressing false alarms according to an embodiment.

FIG. 2 shows a block diagram illustrating an example system 200 for suppressing false alarms according to an embodiment. System 200 includes a plurality of patient monitoring devices 210, specifically N patient monitoring devices, where N is an integer greater than or equal to one. Each patient monitoring device of the plurality of patient monitoring devices 210 includes a sensor and a physiological data source. Specifically, first patient monitoring device 211 includes a first sensor 212 and a first physiological data source 213; second patient monitoring device 221 includes a second sensor 222 and a second physiological data source 223; the Nth patient monitoring device 231 includes an Nth sensor 232 and an Nth physiological data source 233, and so on.

The sensors are placed on or in the vicinity of a patient to be monitored and are configured to read different physiological characteristics of the patient. For example, first sensor 212 may measure the patient's electrocardiogram (ECG), the second sensor 222 may measure the patient's invasive arterial blood pressure (IBP), the Nth sensor 232 may measure the patient's pulse oximetry ($SpO_2$), and so on. Alternatively, the sensors 212, 222, and 232 can monitor other physiological characteristics of a patient. In one embodiment, the same physiological trait (e.g., heart rate) can be determined based on sensing different physiological characteristics (ECG, IBP, $SpO_2$) of the patient, making at least some of the data from the sensors redundant.

The physiological data sources 213, 223, and 233 include software algorithms operable on a computer processing circuit or device (e.g., a microprocessor, a microcontroller, an application-specific integrated circuit (ASIC), etc.) including sufficient memory and interface circuitry to interface with the sensors 212, 222, and 232. Physiological data sources 213, 223, and 233 preferably include algorithms which are operable independent of each other to arrive at one or more physiological data based on signals from respective sensors. The physiological data provided by each of physiological data sources 213, 223, and 233 may include raw data from sensors
212, 222, and 232, filtered data, statistical derivations of data from the sensors 212, 222, and 232, binary flags indicating predetermined conditions are met, or other events or conditions based on signals from the sensors 212, 222, and 232.

In some examples, the physiological data sources 213, 223, and 233 may be implemented as hardware and/or software in the corresponding patient monitoring device 211, 221, or 231 as depicted. However, in other examples, it should be appreciated that one or more of the physiological data source 213, 223, and 233 may be implemented away from the corresponding patient monitoring device 211, 221, or 231. For example, one or more of the physiological data sources 213, 223, and 233 may be implemented in the computing device 240.

Further, in some examples, one or more of the physiological data sources 213, 223, and 233 may be distributed across the corresponding patient monitoring device and the computing device 240 to perform some tasks separately in the patient monitoring device and the computing device. As an illustrative example, a first portion of the first physiological data source 213 may perform pre-processing and encoding in the patient monitoring device 211 while a second portion of the first physiological data source 213 may perform resource-intensive computations in the computing device 240.

The physiological data sources may provide physiological data to the computing device 240 as depicted. Specifically, the computing device 240 may include a plurality of predictor clouds, including a first predictor cloud 241, a second predictor cloud 251, and so on, up to and including an Nth predictor cloud 261. The computing device 240 may include a predictor cloud for each patient monitoring device. For example, first physiological data source 213 is configured to provide a first measurement of a first physiological trait based on a first physiological characteristic to a first predictor cloud 241. Similarly, second physiological data source 223 is configured to provide a second measurement of a second physiological trait based on a second physiological characteristic of the patient to a second predictor cloud 251, while the Nth physiological data source 233 is configured to provide an Nth measurement of an Nth physiological trait based on an Nth physiological characteristic of the patient to a corresponding Nth predictor cloud 261. As described further herein with regard to FIG. 3, each predictor cloud 241, 251, and 261 may include multiple neural networks, specifically a long short-term memory (LSTM) neural network and a recurrent neural network (RNN) stacked in series for estimating or predicting the expected value of a physiological trait responsive to measurements input to the predictor cloud.

The estimates or predictions output by each predictor cloud 241, 251, and 261 are concatenated or otherwise merged into a combined prediction 270. The combined prediction 270 is then input to a dense multilayer perceptron (MLP) 275. In a dense MLP, each node of a hidden layer of the dense MLP is connected to every other node in the next layer.

The output 280 of the MLP 275 may comprise a binary value, for example, true or false, 0 or 1, and so on. Depending on how the MLP 275 is configured, the output 280 determines whether an alarm should be generated or suppressed. In this way, the prediction of physiological parameters of a patient can aid clinicians to achieve better care. An example method for using the output 280 to allow or suppress an alarm generated by a standard alarm method is described further herein with regard to FIG. 4.

FIG. 3 shows a block diagram illustrating an example predictor cloud 300 for analyzing an electronic signal from a patient monitoring device according to an embodiment. More specifically, the time series 305 of an electronic signal $x_n$ is input to a long short-term memory (LSTM) neural network 310 and a recurrent neural network (RNN) 320 to generate a prediction 328.

As noted above, predictor cloud 300 comprises a long short-term memory (LSTM) neural network 310 and a recurrent neural network (RNN) 320 stacked in series. LSTM neural network 310 includes an input layer 312, at least one hidden layer 314, and an output layer 316. The LSTM neural network 310 overcomes the vanishing gradient problem experienced by recurrent neural networks by employing multiplicative gates that enforce constant error flow through the internal states of special units called memory cells. The LSTM neural network 310 thus has the ability to learn the long term correlations in a sequence.

The outputs 318 of the LSTM neural network 310 are input to the RNN 320. RNN 320 may comprise, as a non-limiting example, a gated recurrent neural network. RNN 320 merges the outputs 318 of the LSTM neural network 310 in order to learn and fuse their patterns in longer time slices. In some examples, the RNN 320 may include a pooling and a softmax function. The prediction output 328 output by the RNN 320 comprises a prediction of the electronic signal $x_n$ at the time $t_n$.

FIG. 4 shows a high-level flow chart illustrating an example method 400 for suppressing false alarms according to an embodiment. Method 400 is described herein with reference to the systems and components depicted in FIGS. 1-3, though it should be understood that the method may be implemented with other systems and components without departing from the scope of the present disclosure. For example, method 400 may be implemented as executable instructions in the non-transitory memory of computing device 111.

Method 400 begins at 405. At 405, method 400 receives a plurality of electronic signals corresponding to a measured physiological parameter of a patient. Each electronic signal of the plurality of electronic signals is generated by a patient monitoring device, such as one of the plurality of patient monitoring devices 101.

At 410, method 400 calculates a prediction for each electronic signal. Specifically, each electronic signal of the plurality of electronic signals received at 405 is input to a corresponding predictor cloud configured to predict and estimate the physiological parameter. As described hereinabove with regard to FIGS. 2 and 3, a predictor cloud comprises an LSTM neural network and a recurrent neural network stacked in series. Thus, each of the electronic signals or parameters may be fed simultaneously into a plurality of predictor clouds with different activation and hyper parameter settings in order to learn and predict the physiological parameters.

At 415, method 400 combines the predictions for each electronic signal. In some examples, the predictions output by each predictor cloud may be concatenated or otherwise merged.

At 420, method 400 evaluates the combined predictions for alarm conditions. As an illustrative and non-limiting example, the method may input the combined predictions into a multilayer perceptron (MLP) that determines whether an alarm should be generated based on a model learned from an input vector obtained by concatenation of the predictor clouds' outputs. While an MLP may be preferable in comparison to other types of neural networks due to the relatively higher number of degrees of freedom of the MLP, it should be appreciated that one or more neural networks other than an MLP may be used to evaluated the combined predictions for alarm conditions. Thus, at 420, method 400 evaluates whether alarm conditions are predicted based on the combined predictions from the plurality of predictor clouds.

Continuing at 425, method 400 determines whether a standard monitoring method detects alarm conditions. The standard monitoring method may comprise any suitable method for detecting alarm conditions known in the art; the method described herein of detecting alarm conditions via a plurality of predictor clouds operates in parallel to such a standard monitoring method in order to reduce the number of false positive alarms generated by the standard monitoring method. As an exemplary and non-limiting example, a standard monitoring method may comprise a threshold-based method wherein an alarm is generated responsive to measurements of one or more physiological parameters exceeding threshold limits. Such a method may additionally or alternatively generate an alarm responsive to, as an example, a rate of change of a measurement of a physiological parameter exceeding threshold limits.

Continuing at 430, method 400 determines whether alarm conditions are predicted at 420. If alarm conditions are not predicted ("NO"), method 400 proceeds to 435. At 435, method 400 determines whether alarm conditions are detected by the standard monitoring method at 425. If alarm conditions are detected ("YES"), method 400 continues to 440. At 440, method 400 suppresses the alarm generated by the standard monitoring method. Thus, even though the standard monitoring method detects alarm conditions, an alarm is not generated because the alarm conditions are not predicted. Method 400 then returns.

However, referring again to 435, if alarm conditions are not detected ("NO"), method 400 proceeds to 445. At 445, no alarm is generated, since alarm conditions are neither predicted nor detected. Method 400 then returns.

Referring again to 430, if alarm conditions are predicted based on the combined predictions at 420 ("YES"), method 400 continues to 437. At 437, method 400 determines whether alarm conditions are detected by the standard monitoring method at 425. If alarm conditions are detected ("YES"), method 400 proceeds to 450. At 450, method 400 generates an alarm. In this instance, the alarm is generated because alarm conditions are both predicted and detected. The generated alarm may take on any form including, but not limited to, an audible sound, a visual indicator, and/or a vibrating or otherwise tactile alert. The alarm may include a message indicating the reason for the alarm. The alarm may also be differentiated based on a number of criteria including the type and severity of the event causing the alarm. Method 400 then returns.

However, referring again to 437, if alarm conditions are not detected ("NO"), method 400 continues to 442. At 442, method 400 determines whether an asystole is predicted. Asystole, also referred to as flatline, comprises a state of no electrical activity from the heart and therefore no blood flow. If an asystole is not predicted ("NO"), method 400 proceeds to 445, wherein no alarm is generated and the method returns. Thus, even though alarm conditions are predicted based on the combined predictions from the plurality of predictor clouds, since alarm conditions are not detected by the standard monitoring method and the prediction does not predict an asystole, method 400 does not generate an alarm. However, if an asystole is predicted ("YES"), method 400 proceeds to 450, wherein method 400 generates an alarm. Method 400 thus generates an alarm responsive to an asystole prediction despite the standard monitoring method not detecting alarm conditions. In this instance, the predicted alarm conditions are considered severe enough to override the lack of an alarm generated by the standard monitoring method. Method 400 then returns.

The system architecture described hereinabove consists of different layers of abstraction for each modality or patient monitor. Namely, an LSTM neural network is provided for each channel of each modality. A subsequent layer comprises a gated recurrent neural network that merges outputs of the LSTM in order to learn and fuse their patterns in longer time slices. The last layer of the network comprises a pooling and a softmax function. While such a network is trained in a patient-specific manner, to avoid over-fitting and improve generalization of the model, a cloud of such networks trained individually may then be used to merge and fuse all network outputs. The proposed architecture is thus modular and flexible, and can be adjusted according to the available modalities by fine-tuning the cloud after fixing the inputs.

The systems and methods described herein may be used for different clinical applications, including but not limited to epilepsy prediction and detection, patient activity and state recognition, false alarm suppression and assertion in ICU monitors, and so on. In some examples, the hyper parameters of each predictor cloud may be adjusted and the network architecture adapted for the specific purpose. With supervised learning, the neural networks described herein should learn the underlying model and distribution of inputs according to the annotated ground truth or training data. The methods described herein address major limitations of conventional and classical heuristic-based solutions which are no longer feasible for tackling big data.

A technical effect of the disclosure is the generation of an alarm based on physiological characteristics of a patient. Another technical effect of the disclosure includes the suppression of an alarm based on a deep neural network analysis of patient monitor data.

In one embodiment, a method comprises: inputting each electronic signal of a plurality of electronic signals into a corresponding predictor cloud of a plurality of predictor clouds, each predictor cloud comprising a long short-term memory neural network and a recurrent neural network; and responsive to an alarm generated based on at least one of the plurality of electronic signals, suppressing the alarm responsive to outputs of the plurality of predictor clouds indicating the alarm is false.

In a first example of the method, each electronic signal of the plurality of electronic signals corresponds to a physiological characteristic of a patient. In a second example of the method optionally including the first example, the physiological characteristic includes one of a heart rate, a blood pressure, peripheral oxygen saturation, blood glucose levels, and an electrocardiogram. In a third example of the method optionally including one or more of the first and second examples, the outputs of the plurality of predictor clouds comprise estimates of the plurality of electronic signals. In a fourth example of the method optionally including one or more of the first through third examples, the method further comprises combining the outputs of the plurality of predictor clouds. In a fifth example of the method optionally including one or more of the first through fourth examples, combining the outputs comprises concatenating the outputs of the plurality of predictor clouds. In a sixth example of the method optionally including one or more of the first through fifth examples, the method further comprises inputting the combined outputs into a multilayer perceptron trained to determine if the alarm should be generated based on the combined outputs. In a seventh example of the method optionally including one or more of the first through sixth examples, the method further comprises, responsive to the alarm not generated based on at least one of the plurality of electronic signals while the outputs of the plurality of predictor clouds indicates the alarm is true, generating the alarm. In an eighth example of the method optionally including one or more of the first through seventh examples, one or more electronic signals of the plurality of electronic signals may be added to or removed from the plurality of electronic signals. In a ninth example of the method optionally including one or more of the first through eighth examples, the alarm comprises one or more of a visual alarm, an audio alarm, and a tactile alarm.

In another embodiment, a method comprises receiving a plurality of electronic signals, each electronic signal of the plurality of electronic signals corresponding to physiological measurements of a patient, predicting, for each electronic signal with a corresponding predictor cloud comprising a long short-term memory neural network and a recurrent neural network, an expected value for the electronic signal, concatenating the expected value for each electronic signal into a combined prediction, determining, with a multilayer perceptron, whether to generate an alarm based on the combined prediction, and generating the alarm responsive to output of the multilayer perceptron indicating to generate the alarm.

In a first example of the method, the plurality of electronic signals include one or more of a heart rate, a blood pressure, peripheral oxygen saturation, blood glucose levels, and an electrocardiogram. In a second example of the method optionally including the first example, the alarm comprises one or more of a visual alarm, an audio alarm, and a tactile alarm. In a third example of the method optionally including one or more of the first and second examples, the method further comprises generating a standard alarm responsive to one or more of the electronic signals deviating outside a threshold range, and suppressing the standard alarm responsive to the output of the multilayer perceptron indicating to suppress the alarm. In a fourth example of the method optionally including one or more of the first through third examples, one or more electronic signals of the plurality of electronic signals may be added to or removed from the plurality of electronic signals.

In yet another embodiment, a system comprises: a plurality of patient monitoring devices, each patient monitoring device of the plurality of monitoring devices configured to generate an electronic signal representing a measurement of a physiological parameter of a patient; and a processor communicatively coupled to the plurality of patient monitoring devices and the alarm device, the processor configured with instructions in non-transitory memory that when executed cause the processor to: input each electronic signal received from each of the plurality of patient monitoring devices into a corresponding predictor cloud of a plurality of predictor clouds, each predictor cloud comprising a long short-term memory neural network and a recurrent neural network; and responsive to an alarm generated based on at least one of the electronic signals, suppress the alarm responsive to outputs of the plurality of predictor clouds indicating the alarm is false.

In a first example of the system, the plurality of patient monitoring devices includes one or more of an electrocardiograph, a pulse oximeter, a glucose meter, and a temperature sensor. In a second example of the system optionally including the first example, the system further comprises a display device communicatively coupled to the processor, wherein the processor is further configured with instructions in the non-transitory memory that when executed cause the processor to display, via the display device, the alarm. In a third example of the system optionally including one or more of the first and second examples, the alarm is generated responsive to one or more of the electronic signals deviating outside a threshold range. In a fourth example of the system optionally including one or more of the first through third examples, the processor is further configured with instructions in the non-transitory memory that when executed cause the processor to evaluate the outputs of the plurality of predictor clouds with a multilayer perceptron to determine whether the alarm is false.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a computing device, comprising:
   inputting each electronic signal of a plurality of electronic signals corresponding to measurements of physiological parameters of a patient and acquired via a plurality of patient monitoring sensors into a corresponding predictor cloud of a plurality of predictor clouds stored in non-transitory memory of the computing device;
   estimating a physiological parameter of the physiological parameters via the predictor cloud, each predictor cloud comprising a long short-term memory neural network and a recurrent neural network configured in series, wherein all output of the long short-term memory neural network is input to the recurrent neural network, each predictor cloud corresponding to a different individual sensor of the plurality of sensors;
   concatenating outputs of the plurality of predictor clouds into a combined prediction via concatenation in a string or chain;
   inputting the combined prediction into a multilayer perceptron trained to determine if an alarm should be generated based on the combined prediction;
   determining, with the multilayer perceptron, whether to generate the alarm based on the combined prediction; and
   responsive to the alarm generated based on at least one of the plurality of electronic signals, suppressing the alarm responsive to outputs of the plurality of predictor clouds wherein the combined prediction is less than a threshold indicating the alarm is false.

2. The method of claim 1, wherein the physiological parameter includes one of a heart rate, a blood pressure, peripheral oxygen saturation, blood glucose levels, and an electrocardiogram.

3. The method of claim 1, wherein the outputs of the plurality of predictor clouds comprise estimates of the plurality of electronic signals.

4. The method of claim 1, further comprising, responsive to the alarm not generated based on at least one of the plurality of electronic signals while the outputs of the plurality of predictor clouds indicate the alarm is true, generating the alarm.

5. The method of claim 1, wherein one or more electronic signals of the plurality of electronic signals may be added to or removed from the plurality of electronic signals.

6. The method of claim 1, wherein the alarm comprises one or more of a visual alarm, an audio alarm, and a tactile alarm.

7. A method for a computing device, comprising:
   receiving a plurality of electronic signals from a plurality of sensors, each electronic signal of the plurality of electronic signals corresponding to physiological measurements of a patient;
   predicting, for each electronic signal with a corresponding predictor cloud of a plurality of predictor clouds, an expected value for the electronic signal, each predictor cloud of the plurality of predictor clouds corresponding to a respective, different, individual sensor of the plurality of sensors, each predictor cloud comprising a long short-term memory neural network and a recurrent neural network configured in series, such that all output of the long short-term memory neural network comprises all input to the recurrent neural network, and stored in non-transitory memory of the computing device;
   concatenating the expected value for each electronic signal into a combined prediction via concatenation in a string or chain, the combined prediction comprising expected values for the plurality of electronic signals;
   determining, with a multilayer perceptron, whether to generate an alarm based on the combined prediction; and
   generating the alarm responsive to output of the multilayer perceptron indicating to generate the alarm.

8. The method of claim 7, wherein the plurality of electronic signals includes one or more of a heart rate, a blood pressure, peripheral oxygen saturation, blood glucose levels, and an electrocardiogram.

9. The method of claim 7, wherein the alarm comprises one or more of a visual alarm, an audio alarm, and a tactile alarm.

10. The method of claim 7, further comprising generating a standard alarm responsive to one or more of the electronic signals of the plurality of electronic signals deviating outside a threshold range, and suppressing the standard alarm responsive to the output of the multilayer perceptron indicating to suppress the alarm.

11. The method of claim 7, wherein one or more electronic signals of the plurality of electronic signals may be added to or removed from the plurality of electronic signals.

12. A system, comprising:
   a plurality of patient monitoring devices, each patient monitoring device of the plurality of patient monitoring devices configured to generate an electronic signal representing a measurement of a physiological parameter of a patient; and
   a processor communicatively coupled to the plurality of patient monitoring devices and an alarm device, the processor configured with instructions in non-transitory memory that, when executed, cause the processor to:
      input each electronic signal received from each of the plurality of patient monitoring devices into a corresponding predictor cloud of a plurality of predictor clouds stored in the non-transitory memory and generate an expected value, each predictor cloud corresponding to a different individual patient monitoring device of the plurality of patient monitoring devices, each predictor cloud comprising a long short-term memory neural network and a recurrent neural network configured in series such that all output of the long short-term memory neural network is input to the recurrent neural network;
      concatenate the expected value for each electronic signal into a combined prediction via concatenation in a string or chain, the combined prediction comprising expected values for the plurality of patient monitoring devices;
      input the combined prediction into a multilayer perceptron trained to determine if an alarm should be generated based on the combined prediction;
      evaluate the combined prediction with the multilayer perceptron to determine whether the alarm is false, wherein the alarm is false if the combined prediction is less than a threshold; and responsive to the alarm generated based on at least one of the electronic signals, suppress the alarm responsive to outputs of the plurality of predictor clouds indicating the alarm is false.

13. The system of claim 12, wherein the plurality of patient monitoring devices includes one or more of an electrocardiograph, a pulse oximeter, a glucose meter, and a temperature sensor.

14. The system of claim 12, further comprising a display device communicatively coupled to the processor, wherein the processor is further configured with instructions in the non-transitory memory that, when executed, cause the processor to display, via the display device, the alarm.

15. The system of claim 14, wherein the alarm is generated responsive to one or more of the electronic signals deviating outside a threshold range.

\* \* \* \* \*